US012805959B2

(12) United States Patent
Di Sessa

(10) Patent No.: US 12,805,959 B2
(45) Date of Patent: Nov. 24, 2026

(54) MODULAR MEDICAL DEVICES AND HAPTIC FEEDBACK

(71) Applicant: Azena Medical, LLC, Walnut Creek, CA (US)

(72) Inventor: Alexandre B. Di Sessa, Walnut Creek, CA (US)

(73) Assignee: Azena Medical, LLC, Walnut Creek, CA (US)

( * ) Notice: Subject to any disclaimer, the term of this patent is extended or adjusted under 35 U.S.C. 154(b) by 696 days.

(21) Appl. No.: 18/208,035

(22) Filed: Jun. 9, 2023

(65) Prior Publication Data

US 2024/0407878 A1 Dec. 12, 2024

(51) Int. Cl.

| | |
|---|---|
| ***A61B 34/00*** | (2016.01) |
| ***A61B 17/00*** | (2006.01) |
| ***A61B 90/00*** | (2016.01) |

(52) U.S. Cl.

CPC .... *A61B 34/76* (2016.02); *A61B 2017/00464* (2013.01); *A61B 2017/00477* (2013.01); *A61B 2034/254* (2016.02); *A61B 2090/0805* (2016.02)

(58) Field of Classification Search

CPC .......... A61B 34/76; A61B 2017/00464; A61B 2017/00477; A61B 2034/254; A61B 2090/0805; A61B 18/20; A61B 90/98; A61B 2017/00734; A61B 2017/00876; A61B 2090/0808

See application file for complete search history.

(56) References Cited

U.S. PATENT DOCUMENTS

| | | | | |
|---|---|---|---|---|
| 2009/0247999 | A1* | 10/2009 | Tuan | A61F 9/00831 606/5 |
| 2012/0116363 | A1* | 5/2012 | Houser | A61B 18/1442 606/1 |
| 2013/0197494 | A1* | 8/2013 | Koifman | A61N 5/06 606/17 |
| 2016/0321422 | A1 | 11/2016 | Albright | |
| 2018/0368849 | A1* | 12/2018 | Swensgard | A61B 17/07207 |
| 2022/0354596 | A1* | 11/2022 | Liu | A61B 34/37 |
| 2023/0097981 | A1 | 3/2023 | Sun et al. | |
| 2023/0099922 | A1 | 3/2023 | Sun et al. | |

FOREIGN PATENT DOCUMENTS

| | | | |
|---|---|---|---|
| BR | 102022020006 | A2 | 4/2024 |

* cited by examiner

*Primary Examiner* — Paula J Stice
(74) *Attorney, Agent, or Firm* — Carr & Ferrell LLP

(57) ABSTRACT

Modular medical devices and haptic feedback are disclosed herein. An example device includes a first portion having an energy storage module and a first magnet disposed on a terminal end of the first portion, a second portion having a hall effect sensor and a controller that is configured to determine a procedure type to enable when the first portion and the second portion are connected and the hall effect sensor senses a magnetic field of the first magnet.

18 Claims, 6 Drawing Sheets

MODULAR MEDICAL DEVICES AND HAPTIC FEEDBACK

CROSS-REFERENCE TO RELATED APPLICATIONS

N/A.

TECHNICAL FIELD

This disclosure pertains to medical devices, and more particularly, but not by way of limitation, to medical devices that comprise a two-part assembly that is modular and enables specific procedures; the medical device also provides haptic feedback.

SUMMARY

According to some embodiments, the present disclosure is directed to a device, comprising a first portion comprising: an energy storage module and a first magnet disposed on a terminal end of the first portion; and a second portion comprising: a hall effect sensor; and a controller that is configured to determine a procedure type, attachment type, power selection to enable when the first portion and the second portion are connected and the hall effect sensor senses a magnetic field produced by the first magnet.

According to some embodiments, the present disclosure is directed to a method comprising joining a first portion of a medical device to a second portion of the medical device, the first portion comprising a first magnet, the second portion comprising a hall effect sensor; determining a first type of medical procedure allowed by the first portion; and loading only the medical procedure allowed by the first portion.

BRIEF DESCRIPTION OF DRAWINGS

Exemplary embodiments are illustrated by way of example and not limitation in the figures of the accompanying drawings, in which like references indicate similar elements.

DETAILED DESCRIPTION OF EXAMPLE EMBODIMENTS

Overview

The present disclosure pertains to devices that are two-part assemblies, referred to in combination as a handpiece. For example, the handpiece comprises an attachment portion and a body portion. These handpieces can be used as medical devices to perform medical procedures such as ablation, cutting, cleaning, healing, tissue stimulation and the like. These components are modularized and are associated with distinct medical procedures and power settings. That is, depending on the particular combination chosen, one combination may enable the parameters of a first medical procedure and another combination may enable device parameters for a second procedure. In more detail, the first medical procedure may have parameters selected for a low-power procedure, whereas the second medical procedure may have parameters selected for a higher-power procedure.

In some embodiments, the attachment portion houses a battery and magnets, while the body portion has a hall effect sensor, a display, a controller, and a tip that can be used to deliver a laser to a patient. The attachment portion is associated with a first type of procedure, which in some instances is designated by battery size. When a first type of attachment portion is detached and replaced with a second type of attachment portion having a larger battery, a second type of procedure is enabled. A controller associated with the second portion can sense which type of attachment portion has been attached and can select the type of procedure allowed by that attachment portion. The association of procedure type is not limited to battery size but can be based on any difference between attachment portions. Although it will be understood that certain procedures require more power than others, therefore higher-powered batteries may enable higher-power procedures. It will be understood that while the attachment has been disclosed as a battery, the attachment can include any type of attachment that includes or excludes a battery.

In some embodiments, the type of body portion that is attached enables one or more procedures rather than, or in addition to, being enabled by the attachment portion. For example, an ablation tool enables ablation procedures, while a cutting tool when joined to the attachment portion enables only cutting procedures. In another example, one tool may be used to treat canker sores, while one can be used to treat gingivitis, and the parameters for each of these medical procedures are unique and only enabled when the user connects the body portion. In this way, the user cannot accidentally enable procedures with the wrong tool or tip.

Example Embodiments

Figure 1:
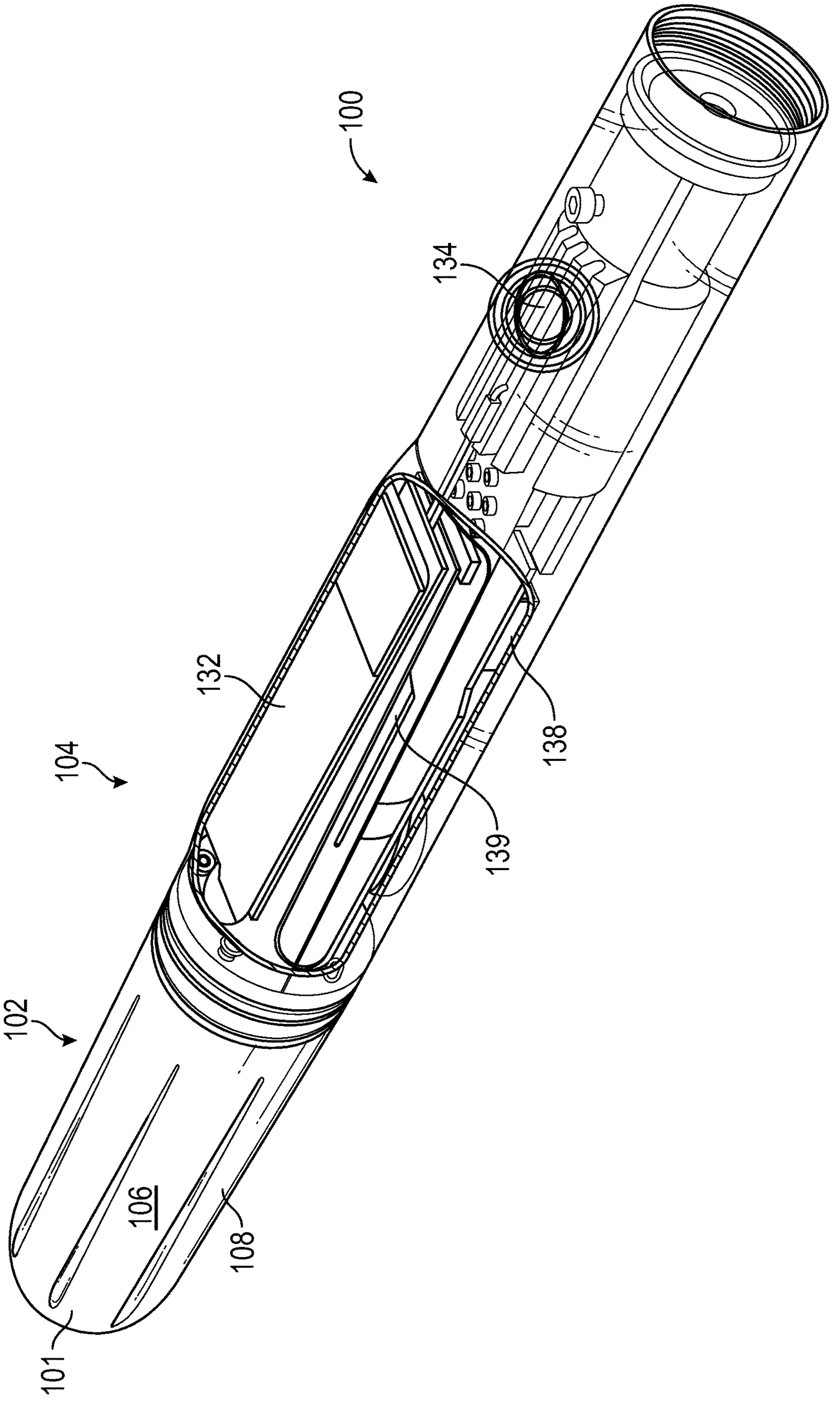
FIG. 1 is an example environment where aspects of the present disclosure can be implemented for use.

Referring now to FIG. 1, which illustrates an example architecture where aspects of the present disclosure are implemented. The example device 100 is a hand-held unit that is comprised of two pieces, an attachment portion 102 (may be referred to as a first portion) and a body portion 104 (may be referred to as a second portion). In some embodiments, the attachment portion 102 includes an electrical energy storage module, such as a battery 106 enclosed in a housing 108.

Figure 2:
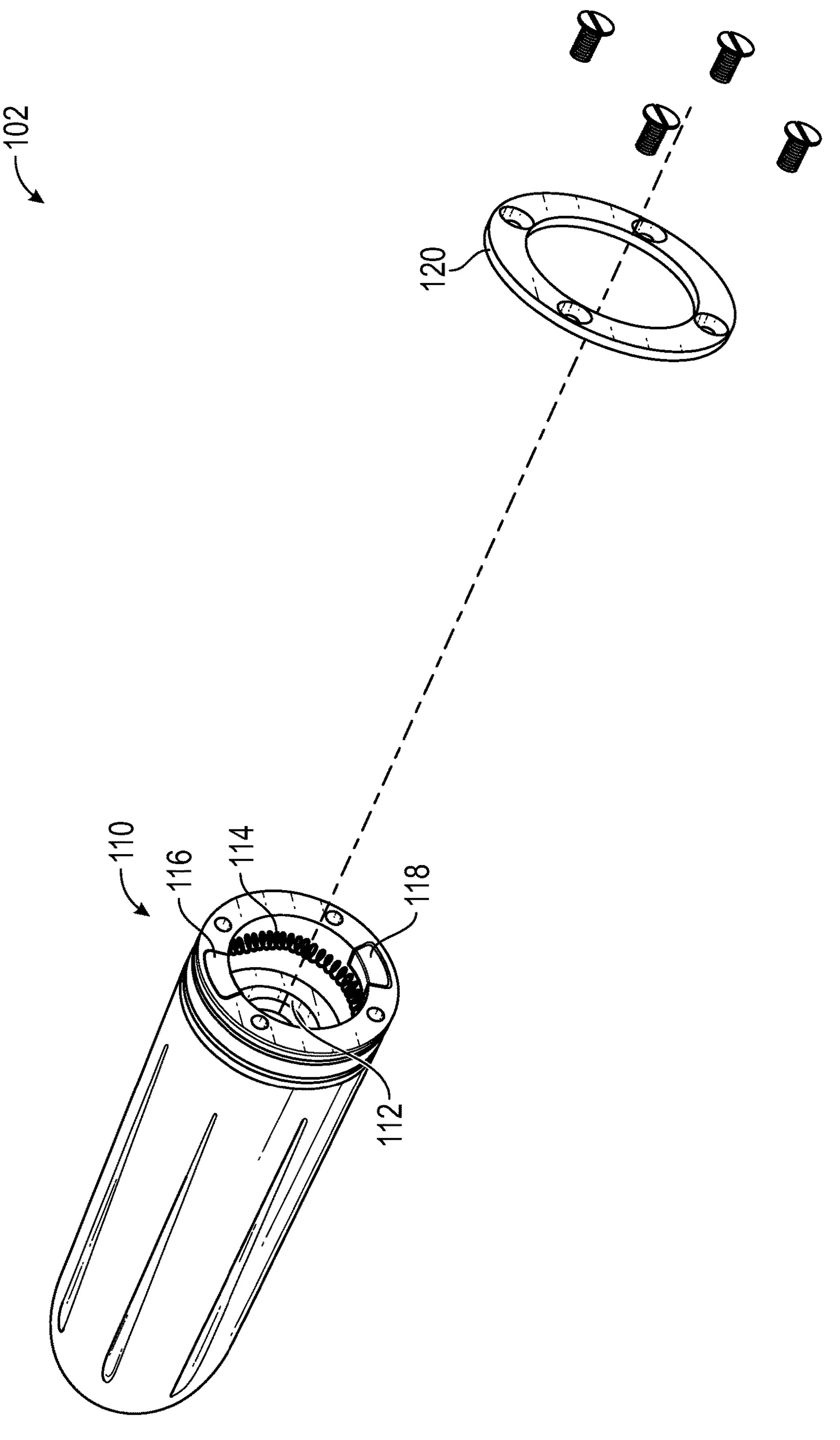
FIG. 2 is an exploded view of an attachment portion.
Figure 3:
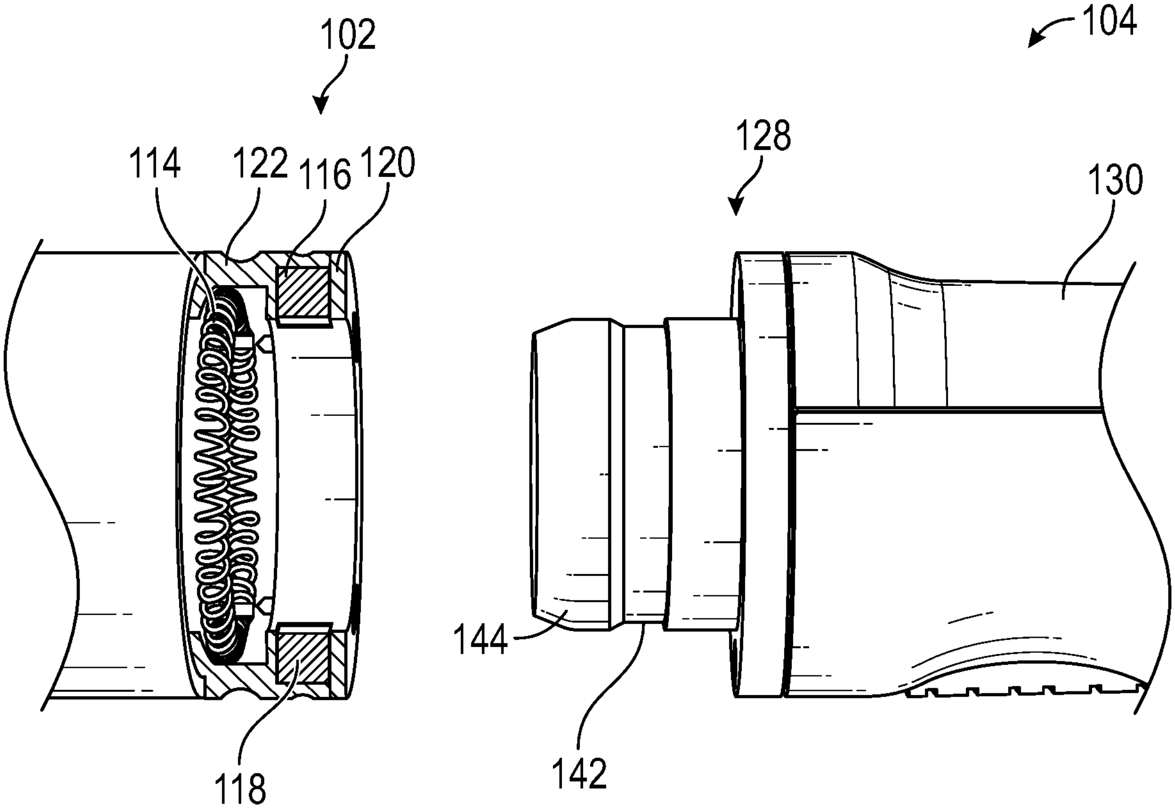
FIG. 3 is a view of the male adapter and a partial cutaway of the terminal end of the attachment portion.

Referring now to FIGS. 1-3 collectively, the attachment portion 102 includes a collar terminal end 110 having a first conductor 112, a resilient element 114, a first magnet 116, a second magnet 118, and a spacer 120. The terminal end 110 has a collar 122 that extends out and forms a female receiver that mates with a male adapter of the body portion 104, as will be discussed in greater detail herein.

The first magnet 116 and the second magnet 118 are located on the terminal end of the collar 122 and are spaced at a 180-degree interval relative to one another, although other spacings and a variety of magnets can be used. The spacer 120 is configured to cover the first magnet 116 and the second magnet 118.

Figure 4:
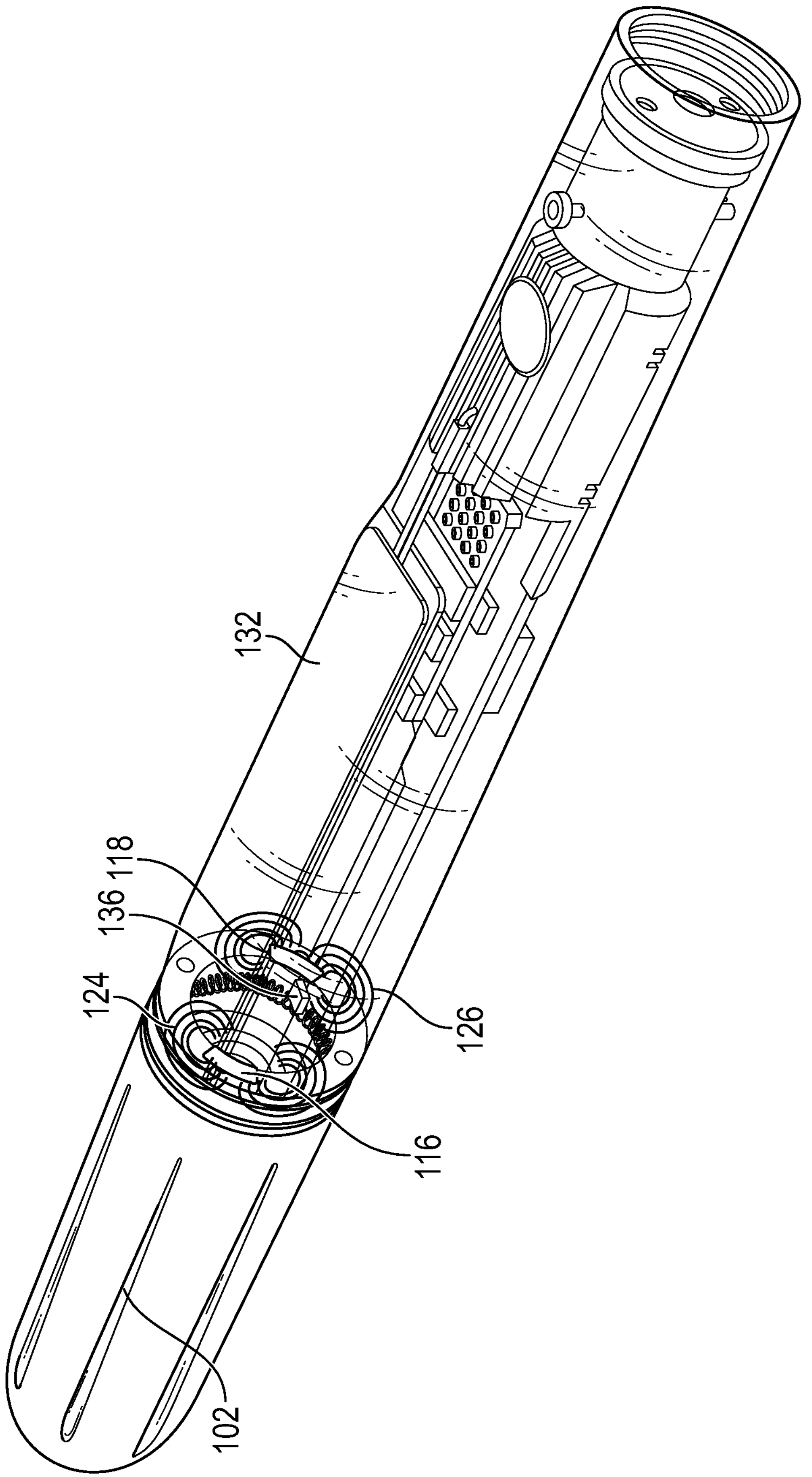
FIG. 4 illustrates magnetic fields interacting with a hall effect sensor.

The first magnet 116 produces a first magnetic field 124 and the second magnet 118 produces a second magnetic field 126 (see FIG. 4 as an example). These magnetic fields are distinguishable from one another by a hall effect sensor integrated into the body portion 104.

The body portion 104 has a male adapter 128, a housing 130, a display 132, a haptic element 134, a hall-effect sensor 136, a controller 138, and a laser source 139. The male adapter 128 is best illustrated in FIG. 3. The male adapter 128 acts as a second conductor that mates with the first conductor 112 when the attachment portion 102 is joined to the body portion 104. When the attachment portion 102 is joined to the body portion 104, components of the body portion 104 can receive energy from the battery 106 such as the display 132, the controller 138, and the haptic element 134. It is noteworthy that the haptic element 134 can be located anywhere inside the body portion 104.

In FIG. 3, the male adapter 128 is a tubular extension that includes a circumferential groove 142 and a tapered end 144. When the attachment portion 102 and the body portion 104 are being joined, the tapered end 144 is inserted into the resilient element 114 and the user continues to push the attachment portion 102 and the body portion 104 together until the resilient element 114 expands and seats into the circumferential groove 142. This action provides a releasable locking force that keeps the attachment portion 102 and the body portion 104 together until separated by the user. The attachment portion 102 and the body portion 104 are shown in association FIG. 3. While in some embodiments, the resilient element 114 is a spring, the resilient element 114 could also be an O-ring, gasket, or the like.

Referring to FIGS. 1-4, the controller 138 comprises a processor and memory. The memory can store instructions that can be executed by the processor to perform various functions. In one example, the controller 138 can detect when an attachment portion is attached. Again, the attachment portion powers the components of the body portion with energy from a battery in the attachment portion. As noted above, each attachment portion can be associated with a procedure type. For example, a first attachment portion can enable an ablation procedure, whereas a second attachment portion can enable a cutting procedure. In some instances, this is tied to the power level of the battery of the attachment portion, but this is not intended to be limiting. In some examples, the power level of two distinct attachment portions is equal, yet they are associated with two different procedures. The user may distinguish two or more different attachment portions by having housings with two different geometrical configurations that have a distinct look and feel to the user. Once the user has selected a procedure or connected an attachment, an indication of procedure is presented on the display 132 as shown in FIG. 4 where Procedure B is displayed. The user can confirm this selection by tapping the display 132, when the display 132 is a touchscreen or capacitive touch device. In another example, the user can confirm the procedure by depressing a button 101 on the attachment portion 102. Another method of selecting a procedure is by turning the attachment portion which will cause the hall effect sensor to show selections on the display. The hall effect sensor not only can detect different attachments, but also can enable selections by twisting the two portions relative to one another. In other embodiments, the user need not confirm; this can occur when the device is capable of enabling only one procedure.

In some embodiments, the controller 138 can determine the power-capacity of the battery by sensing a reference current when the attachment portion is connected. In another example, the type of magnet used or the polarity of the magnet can indicate what type of attachment portion has been attached and what procedures can be enabled.

As noted above, the type of body portion can dictate the type of procedure that is enabled by the controller 138. For example, if the user attaches a cutting tip to the attachment portion, the controller 138 can enable cutting procedures. If the user attaches an ablation tip, the controller 138 can enable ablation procedures.

In some embodiments, what is enabled by the controller 138 are features or parameters of a medical procedure. For example, the controller 138 can detect that the user has attached a body (a tip or tool) that can be used to treat canker sores using laser light generated by the laser source 139. This treatment of canker sores is a distinct medical procedure that requires specific parameters for the laser like wavelength, power, interval, and the like. In one embodiment, when the user attaches a body (a tool or tip) that is used to treat gingivitis, the controller 138 can sense the connection of this tool and tune the laser source 139 to produce a laser with parameters in order to treat that particular condition. Also, it will be understood that while magnets and a hall effect sensor have been described, it is not intended for this to be limiting. The controller 138 can detect the connection between an attachment portion and a body portion using any electrical and/or communicative interface such as an electrical signal, Wi-Fi or BT signals that would be known to one of ordinary skill in the art.

Figure 5:
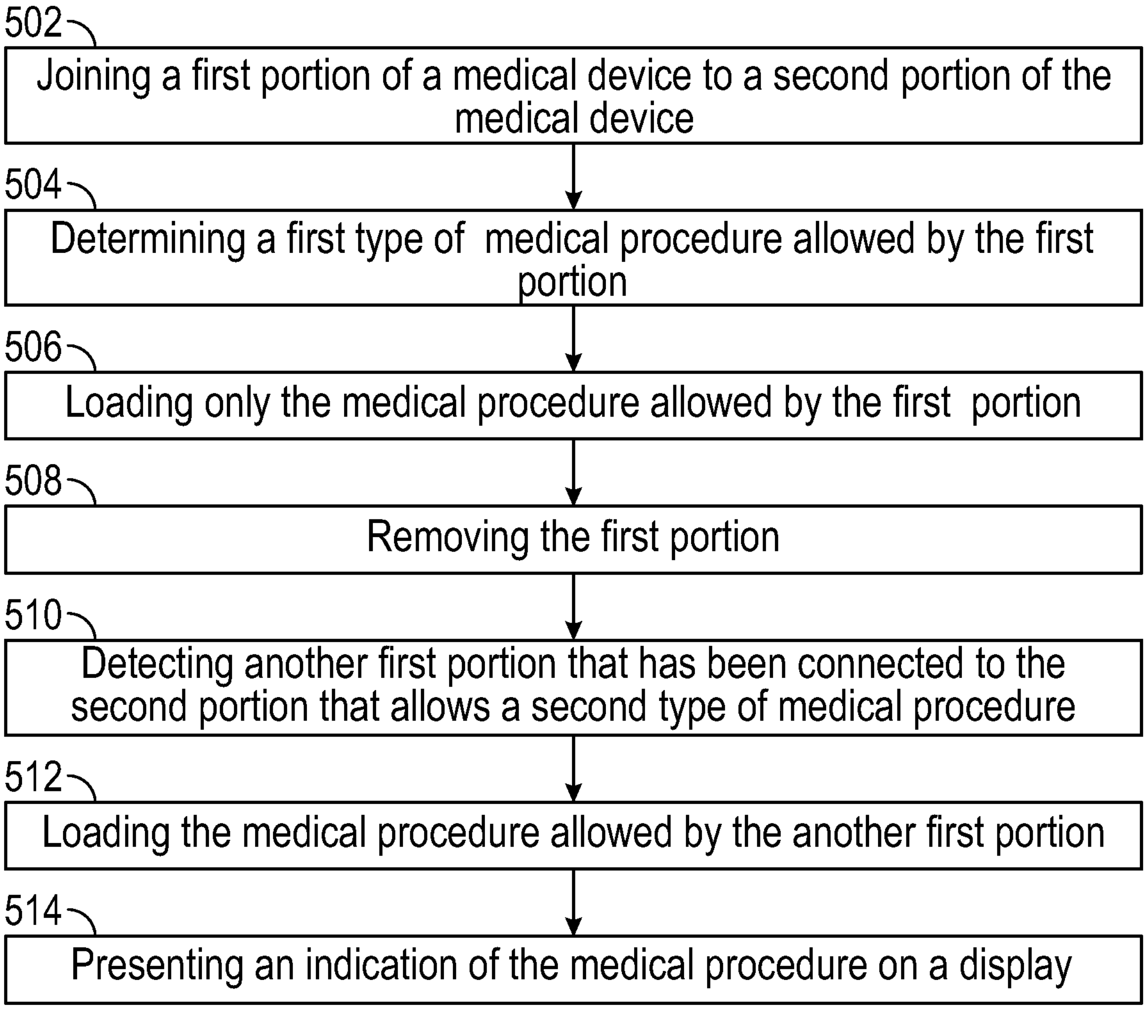
FIG. 5 is a flowchart of an example method.

FIG. 5 is a flowchart of a method of the present disclosure. The method includes a step 502 of joining a first portion of a medical device to a second portion of the medical device, the first portion comprising a first magnet, the second portion comprising a hall effect sensor. Next, the method includes a step 504 of determining a type of attachment that was connected and a first type of medical procedure allowed by the first portion. For example, the first portion can be associated with a medical procedure such as ablation. The method also includes a step 506 of loading only the medical procedure allowed by the first portion. In this instance, the controller loads parameters only for the medical procedure or procedures enabled by the first portion. This limits the user to only particular medical procedures. The method can include a step 508 of removing the first portion, and a step 510 of detecting another first portion that has been connected to the second portion that allows a second type of medical procedure.

In some embodiments, the method includes a step 512 of loading the medical procedure allowed by the another first portion. In one example, the another first portion enables cutting procedures, which were not available to the user when the original first portion was joined in steps 502-506. In some embodiments, this can include a controller selecting parameters for a laser source in accordance with the medical procedure allowed by the first portion or the another first portion when it is detected. In an optional step, the method includes a step 514 of presenting an indication of the medical procedure on a display.

Figure 6:
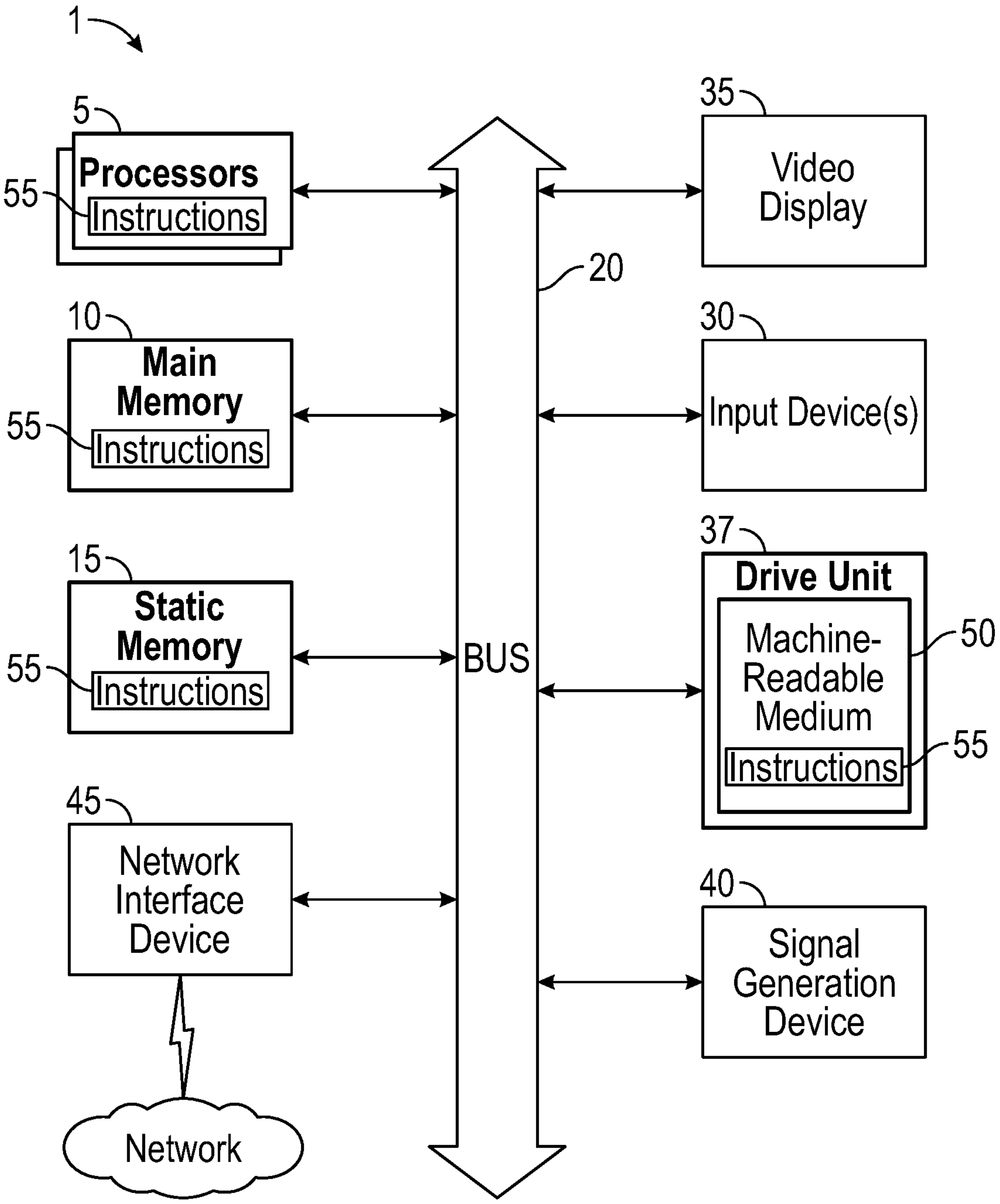
FIG. 6 is a simplified block diagram of a computing system, in accordance with some embodiments.

FIG. 6 is a diagrammatic representation of an example machine in the form of a computer system 1, within which a set of instructions for causing the machine to perform any one or more of the methodologies discussed herein may be executed. In various example embodiments, the machine operates as a standalone device or may be connected.

The computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alpha-numeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or decentralized database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on." "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a." "an" and "the" are intended to include the plural forms as well, unless the context clearly indicates otherwise. The terms "comprises," "includes" and/or "comprising." "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

In this description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

What is claimed is:

1. A device, comprising:
- a first portion, the first portion comprising:
  - an energy storage module; and
  - a first magnet disposed on a terminal end of the first portion; and
- a second portion, the second portion comprising:
  - a hall effect sensor;
  - a laser source; and
  - a controller that is configured to determine a procedure type to enable when the first portion and the second portion are connected and the hall effect sensor senses a magnetic field of the first magnet, the controller being configured to tune the laser source to produce a laser with parameters for the laser including wavelength, power, and interval, in accordance with the procedure type, and
- the controller being further configured to enable the procedure type when the controller receives a confirmation input from a button associated with the first portion.

2. The device according to claim 1, wherein the device includes a second magnet.

3. The device according to claim 1, wherein the controller is configured to:
- detect when the first portion has been removed; and
- detect another first portion that has been connected to the second portion that allows a second type of medical procedure.

4. The device according to claim 3, wherein the controller that is configured to load the second type of medical procedure that is allowed by the another first portion.

5. The device according to claim 3, wherein the controller is configured to present an indication of the medical procedure on a display.

6. The device according to claim 1, further comprising a display that is a touchscreen or a capacitive touch and wherein the display is configured to receive a touch input or the button associated with the first portion is configured to receive a depression input, to confirm a selection.

7. The device according to claim 6, further comprising a haptic element that confirms the selection with a vibration.

8. The device according to claim 1, further comprising a male adapter extending from the second portion, the male adapter comprising a groove.

9. The device according to claim 8, wherein the male adapter is configured to be inserted into the terminal end of the first portion, the first portion comprising a resilient member that sits in the groove of the male adapter when the first portion and the second portion are coupled.

10. The device according to claim 9, wherein the resilient member is a circular spring.

11. A method, comprising:
- joining a first portion of a medical device to a second portion of the medical device, the first portion comprising a first magnet, the second portion comprising a hall effect sensor and a laser source;
- determining a first type of medical procedure allowed by the first portion;
- receiving a confirmation input from a button associated with the first portion;
- tuning the laser source to produce a laser with parameters for the laser including wavelength, power, and interval, in accordance with the first type of medical procedure allowed by the first portion; and
- loading only the medical procedure allowed by the first portion.

12. The method according to claim 11, further comprising:
- removing the first portion; and
- detecting another first portion that has been connected to the second portion that allows a second type of medical procedure.

13. The method according to claim 12, further comprising:
- loading the medical procedure that is allowed by the another first portion; and
- presenting an indication of the medical procedure on a display.

14. The method according to claim 13, further comprising confirming a selection on the display by receiving a touch gesture or confirmation input from the button associated with the first portion.

15. The method according to claim 14, further comprising causing a haptic element to confirm the selection with a vibration.

16. The method according to claim 15, further comprising inserting a male adapter of the second portion into the first portion, the male adapter comprising a groove.

17. The method according to claim 16, further comprising inserting the male adapter into a terminal end of the first portion such that a resilient member in the first portion sits in the groove of the male adapter when the first portion and the second portion are coupled.

18. The method according to claim 16, further comprising:

detecting removal of the first portion;

detecting attachment of another first portion; and selecting parameters for a laser source in accordance with the medical procedure allowed by the another first portion.

* * * * *